(12) United States Patent
Nagale et al.

(10) Patent No.: US 10,315,005 B2
(45) Date of Patent: Jun. 11, 2019

(54) METHODS AND SYSTEMS FOR TREATMENT OF A BLADDER

(71) Applicant: Boston Scientific Scimed, Inc., Maple Grove, MN (US)

(72) Inventors: Sandra Nagale, Bolton, MA (US); David C. Borzelleca, Hudson, MA (US); Michael F. Weiser, Tewksbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 28 days.

(21) Appl. No.: 15/385,301

(22) Filed: Dec. 20, 2016

(65) Prior Publication Data
US 2017/0100565 A1 Apr. 13, 2017

Related U.S. Application Data

(63) Continuation of application No. 14/212,247, filed on Mar. 14, 2014, now Pat. No. 9,555,218.
(Continued)

(51) Int. Cl.
*A61M 25/00* (2006.01)
*A61M 25/10* (2013.01)
*A61M 37/00* (2006.01)

(52) U.S. Cl.
CPC .... *A61M 25/0084* (2013.01); *A61M 25/0074* (2013.01); *A61M 25/1011* (2013.01);
(Continued)

(58) Field of Classification Search
CPC ........ A61M 5/3287; A61M 2025/1013; A61M 2025/1086; A61M 2025/0036; A61M 2025/105; A61M 2025/0085; A61M 2025/0086; A61M 2025/0087; A61M 2025/0096; A61M 25/0084; A61M 25/0074; A61M 25/1011;
(Continued)

(56) References Cited

U.S. PATENT DOCUMENTS 6,692,490 B1 2/2004 Edwards
2003/0171645 A1 9/2003 Silverman et al.
(Continued)

FOREIGN PATENT DOCUMENTS

WO WO 2012/083155 A2 6/2012
WO WO 2013/039711 A2 3/2013

OTHER PUBLICATIONS

"Core Technology," retrieved from Contura website at http://www.contura.com/products/core-technology on Dec. 28, 2012 (2 pages).
(Continued)

*Primary Examiner* — Imani N Hayman
*Assistant Examiner* — Tiffany Legette
(74) *Attorney, Agent, or Firm* — Bookoff McAndrews, PLLC

(57) ABSTRACT

A medical device is disclosed. The medical device may include an elongate member having a proximal end and a distal end an expandable end effector assembly extending distally from the distal end of the elongate member. The end effector assembly may include a plurality of end effector units each having an injector for simultaneously delivering material into tissue.

20 Claims, 16 Drawing Sheets

Related U.S. Application Data

(60) Provisional application No. 61/799,260, filed on Mar. 15, 2013.

(52) U.S. Cl.
CPC .............. *A61M 2025/0036* (2013.01); *A61M 2025/0086* (2013.01); *A61M 2025/0087* (2013.01); *A61M 2025/105* (2013.01); *A61M 2025/1013* (2013.01); *A61M 2025/1086* (2013.01); *A61M 2037/0023* (2013.01); *A61M 2210/1085* (2013.01)

(58) Field of Classification Search
CPC .. A61M 2025/0037; A61M 2210/1085; A61M 2210/1088
See application file for complete search history.

(56) References Cited

U.S. PATENT DOCUMENTS

| | | | |
|---|---|---|---|
| 2004/0138643 A1* | 7/2004 | Seward | A61L 29/16 604/507 |
| 2006/0190022 A1 | 8/2006 | Beyar et al. | |
| 2006/0247720 A1 | 11/2006 | Starkebaum | |
| 2007/0173786 A1* | 7/2007 | Recinella | A61M 25/0026 604/523 |
| 2007/0282184 A1 | 12/2007 | Roberts | |
| 2008/0125709 A1 | 5/2008 | Chang et al. | |
| 2009/0012469 A1 | 1/2009 | Nita | |
| 2009/0216204 A1* | 8/2009 | Bhavaraju | A61M 35/00 604/290 |
| 2010/0152704 A1 | 6/2010 | Lee et al. | |
| 2010/0198139 A1 | 8/2010 | Glickman | |
| 2010/0256594 A1 | 10/2010 | Kimmell et al. | |
| 2010/0268191 A1 | 10/2010 | Trudel et al. | |
| 2011/0166516 A1 | 7/2011 | Orr | |
| 2013/0018281 A1 | 1/2013 | Nagale et al. | |
| 2013/0072855 A1 | 3/2013 | Sherry et al. | |
| 2013/0090640 A1 | 4/2013 | Nagale et al. | |
| 2013/0090648 A1 | 4/2013 | Nagale et al. | |
| 2013/0331783 A1* | 12/2013 | Herman | A61M 25/10 604/103.08 |

OTHER PUBLICATIONS

Hillel, Alexander T. et al., "Photoactivated Composite Biomaterial for Soft Tissue Restoration in Rodents and in Humans," Science Translational Medicine, vol. 3, Iss. 93, p. abstract & 1-12 (2011) (13 pages).

Karajanagi, Sandeep S. et al., "Assessment of Canine Vocal Fold Function After Injection of a New Biomaterial Designed to Treat Phonatory Mucosal Scarring," Annals of Otology, Rhinology & Laryngology, vol. 120, pp. 175-184 (2011), Abstract only (1 page).

Xing, Jinhong et al., "Alterations of Gastrointestinal Motility in Obesity" Obesity Research vol. 12 No. 11, Nov. 2004, p. 1723-1732 (10 pages).

Fidia Farmaceutici SpA—Tissue Repair, "Products: Tissue Repair," retrieved from Fidia website at http://www.fidiapharma.com/files/index.cfm?id_rst=137 on Dec. 28, 2012 (3 pages).

Foschi, D. et al., "Treatment of morbid obesity by intraparietogastric administration of botulinum toxin: a randomized, double-blind, controlled study" International Journal of Obesity (2007) 31, p. 707-712 (6 pages).

\* cited by examiner

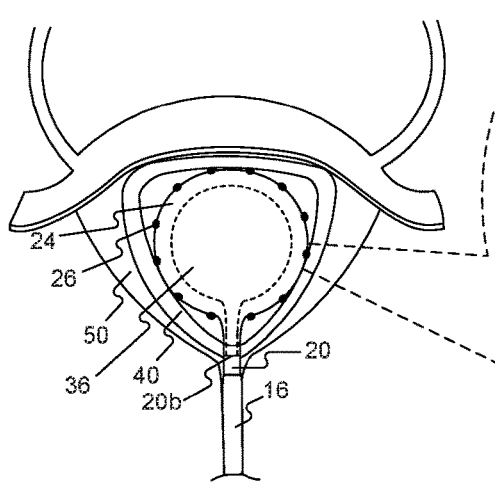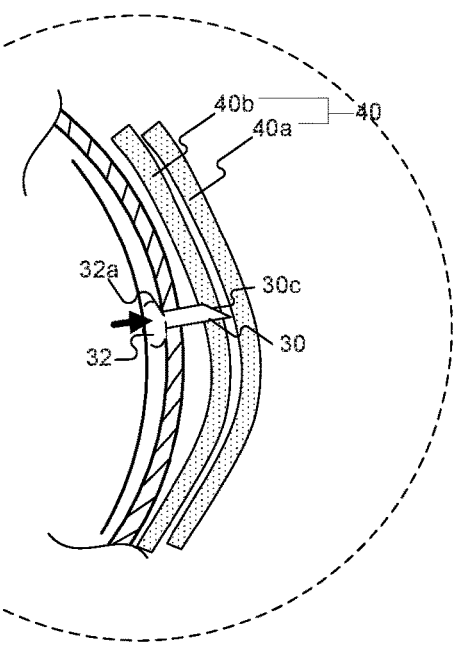
FIG. 7D
FIG. 7E

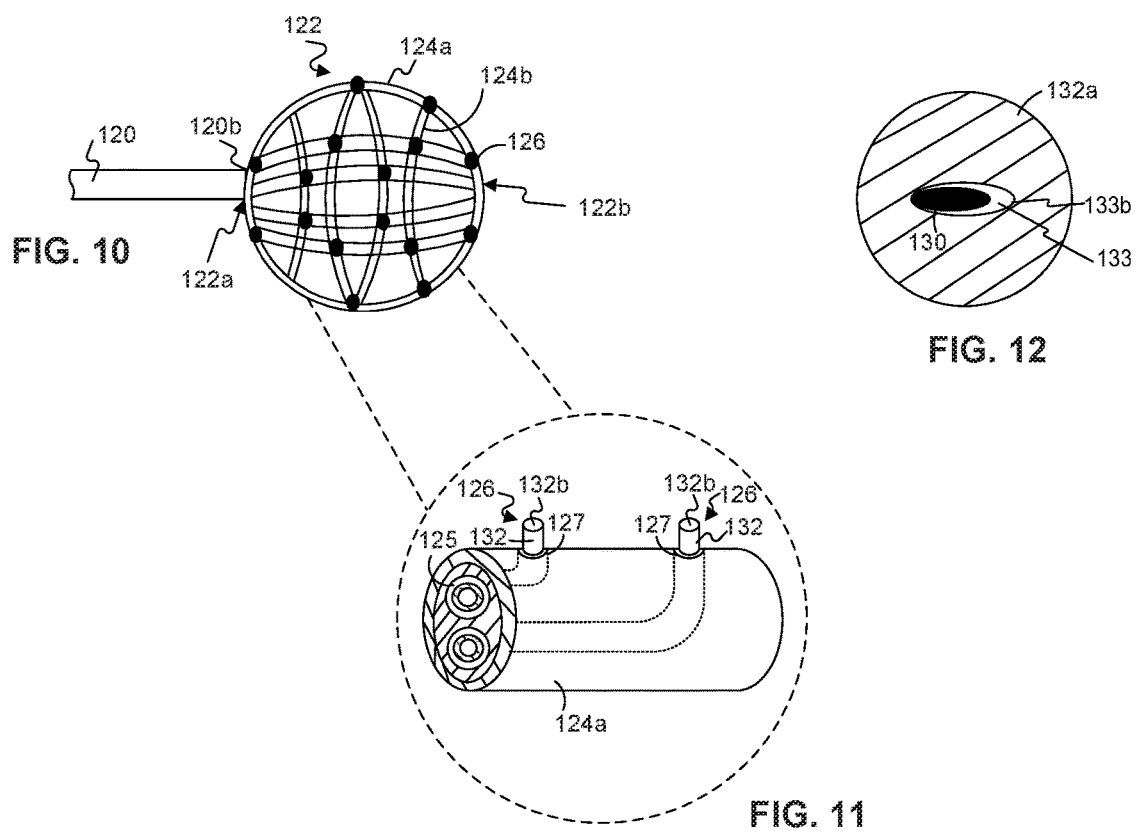

METHODS AND SYSTEMS FOR TREATMENT OF A BLADDER

CROSS-REFERENCE TO RELATED APPLICATION

This application is a continuation application of U.S. patent application Ser. No. 14/212,247, filed Mar. 14, 2014, which claims the benefit of U.S. Provisional Application No. 61/799,260, filed Mar. 15, 2013, the disclosures of each are incorporated herein by reference in their entirety.

BRIEF DESCRIPTION

Field

Embodiments of this disclosure relate generally to methods and systems for treating a bladder within a patient. In particular, embodiments of the present disclosure relate to methods and systems for treating bladder overactivity.

Background

Overactive Bladder (OAB) is a urological condition that affects approximately 50 million patients worldwide. A patient suffering from OAB typically experiences sudden yet frequent and unstoppable urges to urinate, even though the bladder may contain only a small amount of urine. This condition is usually associated with frequent and spontaneous contractions of the detrusor muscle, which is located in the bladder wall and surrounds the bladder.

The etiology of OAB is unclear, and indeed there may be multiple possible causes. OAB, however, is most often associated with detrusor muscle overactivity (i.e., frequent and spontaneous contractions of the detrusor muscle). These frequent contractions may fuse into a global and sustained contraction resulting in an urge to urinate. A malfunctioning detrusor muscle may cause overactive bladder. Indeed, there is a body of evidence suggesting that, in comparison with healthy bladders, overactive bladders exhibit localized changes in detrusor muscle morphology. These changes likely originate from defects on cellular and multi-cellular levels and changes in the nervous system. Such nervous system changes have been correlated to the observed local pathological changes in the muscle (e.g., patchy denervation, increased amount of connective tissue between muscle bundles) which may contribute to the abnormal function of the detrusor muscle.

Identifiable underlying causes include the following: nerve damage caused by abdominal or pelvic trauma or surgery, bladder stones, drug side effects, and neurological disease (e.g., multiple sclerosis, Parkinson's disease, stroke, and spinal cord lesions).

Recent evidence suggests that the detrusor muscle may be triggered by chemicals released from the bladder wall when the wall experiences stimulation, including, but not limited to, stretching of the bladder wall or the presence of potassium or a composite/fluid having a specific pH level, all of which may be associated with increasing accumulation of urine. The released chemicals may include adenosine triphosphate, prostaglandins, nitric oxide, and acetylcholine. The release of these chemicals has been linked to over expression of multiple receptors (muscarinic and cholinergic receptors, TRPV, etc.).

Current therapies for OAB include a variety of approaches. Non-invasive procedures include first-line behavioral and medical therapies employing a class of systemic drugs called anticholinergics. For patients who do not react well to drugs, invasive procedures such as neural stimulation or surgery can be more effective. Both invasive and non-invasive treatments target overall bladder function and do not address local or anatomical abnormalities. Recent studies, however, suggest that abnormal activity may originate from one or more distinct anatomical areas of the bladder such as the dome, internal sphincter, or trigone. Therefore, there exists a need for medical devices and methods of treatment capable of identifying and providing therapy to specific areas of the bladder.

SUMMARY

Embodiments of the disclosure provide methods and systems for treatment of a bladder.

One embodiment of the invention is directed to a medical device. The medical device may include an elongate member having a proximal end and a distal end. The medical device may further include an expandable end effector assembly extending distally from the distal end of the elongate member. The end effector assembly may include a plurality of end effector units each having an injector for simultaneously delivering material into tissue.

In various embodiments, the medical device may include one or more of the following additional features; wherein the injector induces a distal portion that penetrates the tissue to inject material at a predetermined depth; wherein the end effector assembly further includes a dispenser coupled to the injector, the fluid dispenser being an elastomeric fluid container configured to retain the material and rupture upon application of pressure to the fluid container; wherein each end effector unit includes an injection mechanism configured to exert a force on the dispenser to collapse the dispenser and deliver the material into the injector; wherein the expandable end effector assembly includes a first expandable member configured to expand to an expanded configuration, and wherein the injection mechanism includes a second expandable member configured to expand from a partially collapsed configuration to an expanded configuration when the first expandable member is in the expanded configuration within the first expandable member, when the first expandable member is in the expanded configuration so as to exert force on the dispensers; wherein each end effector unit includes an injector positioning mechanism configured to drive the injector into tissue; wherein the injector positioning mechanism includes a first arm and a second arm connected to the first arm via a pivot, wherein the injector is provided on the first arm; wherein the injector positioning mechanism includes: a housing having a closed top, an open bottom, and a space therebetween, at least one magnetic structure disposed within the space configured to move relative to the housing between the closed top and the open bottom, wherein an electromagnetic force is applied to the at least one magnetic structure to move the at least one magnetic structure towards the open bottom of the housing and drive the injector into tissue.

Another embodiment of the invention is directed to a device for treating a bladder. The device may include an elongate member having a proximal end, a distal end, and one or more lumens. The device may further include an end effector assembly extending distally from the distal end of the elongate member. The end effector assembly may define a plurality of apertures. Each aperture may be in communication with a corresponding lumen of the elongate member. An injection unit may be fixed in each aperture of the end effector assembly to direct delivery of material from the end effector assembly.

In various embodiments, the device may include one or more of the following additional features: wherein each injection unit includes a catheter having a distal facing surface defining an aperture and a lumen extending proximally of the aperture, wherein the lumen is configured to receive an injector; wherein the injector is movable relative to the aperture between a retracted position and a deployed position, the injector being configured to deliver material between a first tissue layer and a second tissue layer of the bladder in the deployed position; wherein the injector is movable between a first position and a second position in the deployed position to position the injector between the first tissue layer and the second tissue layer; wherein the distal facing surface includes a ramp adjacent tie aperture for driving the injector between the first position and the second position; wherein the ramp is disposed in a plane that is not perpendicular to a longitudinal axis of the catheter; wherein the injector includes an aligning member configured to orient the injector relative to the catheter.

Another embodiment of the invention is directed a method of treating an organ of a patient. The method may include inserting a medical device within the organ. The medical device may include an elongate member having a proximal end and a distal end, and an end effector assembly extending distally from the distal end of the elongate member. The end effector assembly may include a plurality of end effectors each having an injector for delivering material between two tissue layers of an organ wall. The method may further include expanding the end effector assembly and injecting a material to separate a first layer of tissue from a second layer of tissue.

In various embodiments, the device may include one or more of the following additional features: wherein the first layer of tissue is the mucosal layer, and wherein the second layer of tissue is the detrusor layer; wherein the step of injection a material includes injecting the material through the injectors of all the end effector units; further including inserting the injector into the bladder wall to inject material at a predetermined depth; and further including detecting a location of abnormal function and injecting the material at the location.

Additional objects and advantages of the disclosure will be set forth in part in the description, which follows, and in part will be evident from the description, or may be learned by practice of the disclosed subject matter. The objects and advantages of the disclosed subject matter will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION Of THE DRAWINGS

The accompanying drawings, which are incorporated in and constitute a part of this specification, illustrate embodiments of the disclosure and together with the description, serve to explain the principles of the disclosure. Wherever-possible, the same reference numbers will be used throughout the drawings to refer to the same or like parts.

FIG. 7D illustrates a second expandable member of the end effector assembly being inflated in the first expandable member;

FIG. 7E illustrates an injection of material between two tissue layers of the bladder wall;

FIG. 10 is a side view of an end effector assembly of the medical device of FIG. 8, according to a second embodiment of the disclosure:

FIG. 11 is an exploded view of a portion of a leg of the end effector assembly of FIG. 10;

FIG. 12 is an end view of a catheter of an infection unit feed in an exit aperture on the leg shown in FIG. 11;

FIG. 15A-E illustrate alternative configurations of the end effector assembly of the medical device of FIG. 8, according to embodiments of the disclosure;

DESCRIPTION

Figure 1:
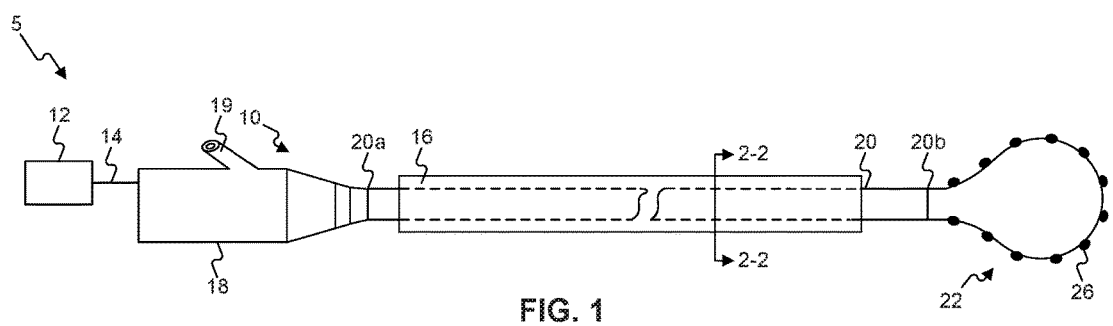
FIG. 1 illustrates a system for treatment of a bladder having a medical device, according to an embodiment of the disclosure.

Reference will now be made in detail to embodiments of the disclosure, examples of which are illustrated in the accompanying drawings.

Embodiments of the disclosure relate generally to systems and methods for treating a bladder within a patient. More particularly, embodiments of the disclosure relate to systems and methods for treating bladder overactivity. Bladder overactivity is characterized by involuntary contractions of the detrusor muscle during bladder filling, which result in a sudden urge to urinate. The disclosed embodiments include systems and methods for treating bladder overactivity by a hydro-dissection procedure, which separates the muscarinic and cholinergic receptors located in the mucosa (e.g., the urothelial and mucosal layers) from the detrusor muscle by injecting a compound into certain areas of the urinary bladder wall. The injected compound may be saline or a similar inert compound, in the form of a fluid or get other applications that disclose methods for treating bladder overactivity by hydro-dissection include U.S. Provisional Patent Application No. 61/535,710, filed Sep. 16, 2011, and U.S. Provisional Patent Application No. 61/677,590, filed Jul. 31, 2012, all of which are incorporated herein by reference in their entirety.

Those skilled in the art will understand that systems and methods described herein may be used to treat conditions of the bladder other than bladder overactivity such as, for example, bladder sphincter dyssynergia, stress incontinence, or painful bladder syndrome (interstitial cystitis). In addition, the same systems and methods may be employed in treating other organs such as, for example, the esophagus, stomach, intestines, colon, or the oral cavity, without departing from the scope of the present disclosure.

FIG. illustrates an exemplary system 5 according to an embodiment of the present disclosure. System 5 includes a medical device 10, at least one fluid source 12 connected to medical device 10 by way of at least one fluid conduit 14, and an outer sheath 18 surrounding at least a portion of medical device 10. For purposes of this disclosure, outer sheath 18 may he constructed from an insulating polymer material such as polyamide, polyurethane, or any other suitable material.

Medical device 10 includes an elongate member 20, a handle portion 18, and an end effector assembly 22. Elongate member 20 has a proximal end 20a and a distal end 20b. For purposes of this disclosure, "proximal" refers to the end closer to the device operator during use, and "distal" refers to the end further from the device operator during use.

Handle portion 18 is disposed at proximal end 20a of elongate member 20 and end effector assembly 22 is disposed at distal end 20b of elongate member 20. End effector assembly 22 includes one or more injection units 28 for delivering material to tissue layers of a bladder.

Figure 2:
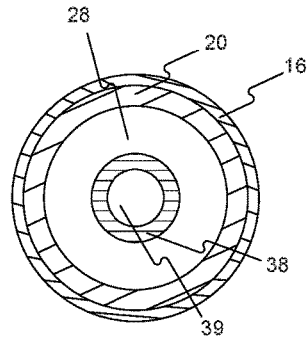
FIG. 2 is a cross-section of the medical device along line 2-2 of FIG. 1.

FIG. 2 is a cross-section of elongate member 20 along lines 2-2 in FIG. 1. Elongate member 20 is a solid rod or tube, made from any suitable biocompatible material known to one of ordinary skill in the art having sufficient flexibility to traverse an anatomical lumen such as a urethra. Such materials may include, but are not limited to, rubbers silicon, synthetic plastics, stainless steel, metal-polymer composites, and metal alloys of nickel, titanium, copper cobalt, vanadium, chromium, and iron. In one embodiment, the material forming elongate member 20 may be a superelastic material such as nitinol, which is a nickel-titanium alloy. Elongate member 20 may have any cross-sectional shape and/or configuration and may be any desired dimension that can be received in the urethra and/or other portions of the urinary tract. Elongate member 20 includes at least one lumen 28 extending from proximal end 20a of the elongate member 20 to distal end 20b of the elongate member 20 for passage of fluid and/or tools to end effector assembly 22.

Figure 3A:
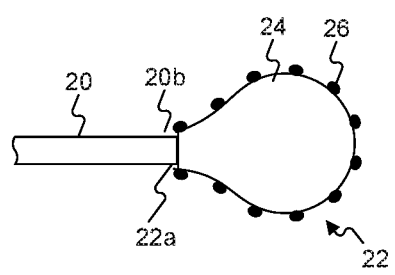
FIG. 3A is a side view of an end effector assembly of the medical device of FIG. 1, the end effector assembly including a first expandable member in a partially collapsed configuration, according to an embodiment of the disclosure.
Figure 3B:
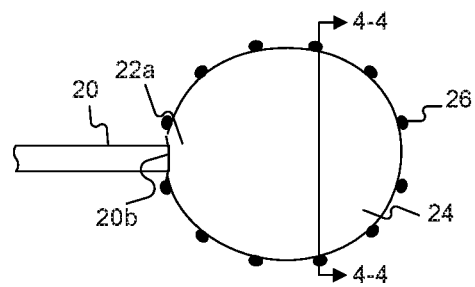
FIG. 3B is a side view of the end effector assembly of FIG. 3A, with the first expandable member in the expanded configuration.

Referring to FIGS. 3A and 3B, end effector assembly 22 includes a first expandable member 24. The phrase "expandable member" generally relates to any expandable structure, such as a balloon or other inflatable structure, regardless of the elasticity of the material comprising the structure. For example, the phrase "expandable member" may denote a thin-walled structure made of material of low elasticity (which does not stretch significantly during inflation) or highly elastic material (which does stretch significantly during inflation). For example, first expandable member 34 may be made from polyethylene terephthalate (PET), polyurethanes, polyethylenes and ionomers, copolyesters, rubbers, polyamides, silicone, latex, or any other suitable materials known in the art.

First expandable member 24 may be made integral with elongate member 20 through connection of a proximal end 22a of the end effector assembly 22 to a region of elongate member 20, such as distal end 20b of elongate member 20. The connection at proximal end 22a of end effector assembly 22 may be accomplished through any suitable means of fixedly connecting end effector assembly 22 to elongate member 12. For example, possible connections may include, but are not limited to, welding, soldering, and/or crimping.

First expandable member 24 may be in fluid communication with lumen 28 of elongate member 20. Lumen 28 may provide a fluid pathway through which a fluid, such as a liquid or gas, may pass to expand (inflate) and contract or collapse (deflate) first expandable member 24. The inflation fluid may be air, water, carbon dioxide, saline solution, or a contrast agent. In alternative embodiments; first expandable member 24 may be mechanically, electrically, or pneumatically expanded and collapsed without departing from the scope of the disclosure.

FIG. 3A shows first expandable member 24 in a partially collapsed configuration, and FIG. 3B shows first expandable member 24 in an expanded configuration. The particular expanded exterior configuration of first expandable member 24, such as the volume, width, radius, length, or other dimension, may be selected so that first expandable member 24 substantially fills the interior of a bladder in the expanded configuration to position the one or more injection units 28 adjacent a bladder wall. For example, in the embodiment shown in FIG. 3B, first expandable member 24 in its expanded configuration may be substantially spherical in shape. It is understood that the outer profile of first expandable member 24 may have an oval, elliptical, square, rectangular or any other shape known to one skilled in the art.

Figure 4:
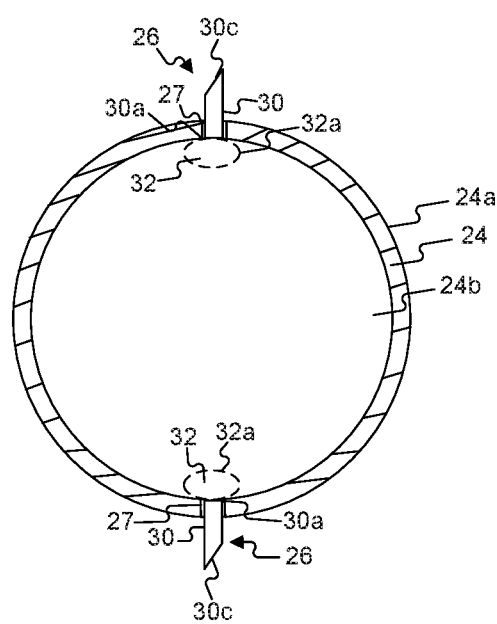
FIG. 4 is a cross-section of the end effector assembly along line 4-4 of FIG. 3B.

The one or more injection units 26 may be uniformly distributed on first expandable member 24 in the partially collapsed configuration and the expanded configuration. First expandable member 24 may act as a positioning mechanism to position the one or more injection units 28 adjacent the bladder wall. Although the depicted embodiment includes twelve injection units 28, end effector assembly 22 may include a greater or lesser number of infection units 28. Referring to FIG. 4, each individual injection unit 28 may be fixed in an exit aperture 27 on first expandable member 24 and extend outwardly of an exterior surface 24a of first expandable member 24.

Each individual injection unit 28 includes an injector 30. Injector 30 may be a conventional needle, including, for example, a micro-needle, having a proximal end 30a, a sharpened distal point 30c, and a hollow interior. Injector 30 may be provided within exit aperture 27 with proximal end 30a of injector 30 positioned within an interior space 24b of first expandable member 24, and distal point 30c extending outwardly of exterior surface 24a of first expandable member 24. The portion of injector 30 within exit aperture 27 may be fixed to exit aperture 27 by welding, soldering, and/or crimping. First expandable member 24 may be a positioning mechanism configured to position each individual injector unit 26 adjacent the bladder wall as first expandable member 24 expands from the partially collapsed configuration to the expanded configuration.

Injector 30 may have any size, shape, and/or configuration, in the exemplary embodiment, injector 30 may have a generally cylindrical shape. The particular dimensions of injector 30, such as the length and/or diameter, may be selected to penetrate tissue and deliver materials at a predetermined depth. In particular, injector 30 may be dimensioned to enter a bladder wall as deep as the mucosa-detrusor junction without penetrating the detrusor muscle. It is contemplated that injector 30 may have any other shape and/or configuration that may accommodate the desired depth.

A dispenser 32 may be a part of injector 30 and may be positioned adjacent proximal end 30a of injector 30 within interior space 24b of first expandable member 24. Dispenser 32 may be a fluid container configured to retain material for injection between tissue layers of a bladder. The material may be saline or a similar inert compound, or in the form of a fluid, gas, gel, or composite fluid. In some embodiments, the material may be a hydrogel.

In the exemplary embodiment, dispenser 32 may be a fluid bulb having an impermeable membrane. In other embodiments, dispenser 32 may be an elastomeric container. In alternative embodiments, dispenser 32 may have a housing, and at least a portion of the housing may have a collapsible wall. In each of these embodiments, dispenser 32 may be positioned adjacent proximal end 30a of injector 30 so that, as the dispenser collapses and/or ruptures, the material may he delivered into an opening at proximal end 30a of injector 30 for delivery to tissue via an opening at distal point 30c.

Figure 5A:
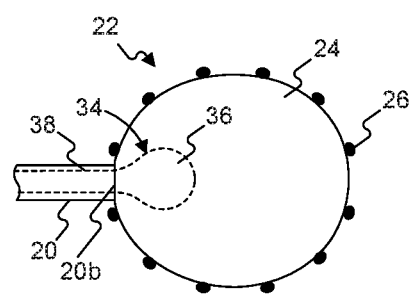
FIG. 5A is a side view of the end effector assembly of FIG. 3B, the end effector assembly including a second expandable member in a collapsed configuration.
Figure 5B:
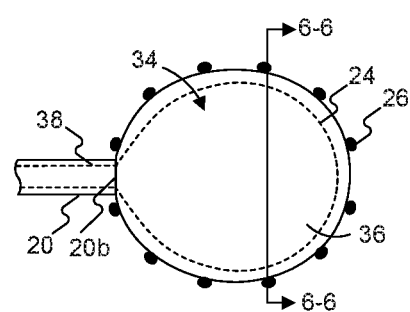
FIG. 5B is a side view of the end effector assembly of FIG. 5A with the second expandable member in the expanded configuration.

Referring now to FIGS. 5A-5B, an injection mechanism 34 may be positioned within first expandable member 24 adjacent to distal end 20b of elongate member 20. The phrase "injection mechanism" generally relates to any known structure or mechanism configured to exert a force on dispenser 32 or a like fluid reservoir so as to deliver the material from dispenser 32 into injector 30 for delivery into the tissue. In this embodiment, injection mechanism 34 includes a second expandable member 38. Second expandable member 36 is connected to a tube 38 which extends proximally through lumen 28 of elongate member 20. In some embodiments, tube 39 may be operably connected to an actuator (not shown) on handle portion 18 and may be movable relative to elongate member 20 in order to advance second expandable member 38 from a refracted position within lumen 28 of elongate member 20 to a deployed position distally of distal end 20b of elongate member 20. In other embodiments, injection mechanism 34 may be inserted into lumen 28 of elongate member 20 via a port 19 (FIG. 1) on handle portion 18, and may be manually deployed and/or retracted.

Tube 38 includes a lumen 39 in fluid communication with the same and/or different fluid source 12. Lumen 39 provides a fluid pathway for a fluid, such as a liquid or gas, to pass to expand (inflate) and contract or collapse (deflate) second expandable member 36. FIG. 5A shows second expandable member 38 in a partially collapsed configuration, and FIG. 5B shows second expandable member 24 in an expanded configuration. The particular expanded, exterior configuration of second expandable member 36, such as the volume, width, radius, length, or other dimension, may be selected so that second expandable member 38 substantially fills the volume within interior space 24b of first expandable member 24.

Figure 6:
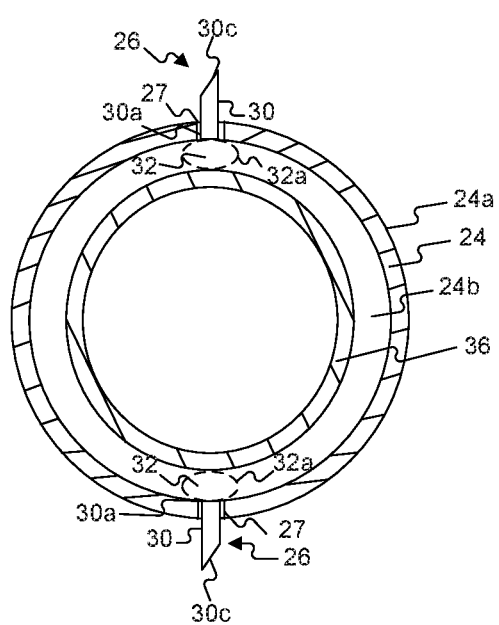
FIG. 6 is a cross-section of the end-effector assembly along line 6-6 of FIG. 5B.

FIG. 6 is a cross-section of end effector assembly 22 along lines 6-6 in FIG. 5B. As shown in FIG. 6, when second expandable member 38 is expanded to the expanded configuration, second expandable member 36 may exert a force on dispenser 32. Upon further expansion of second expandable member 36, pressure may rise on dispenser 32 and rupture impermeable membrane 32a. The material may then be introduced into injector 30 for delivery through distal point 30c.

Figure 7A:
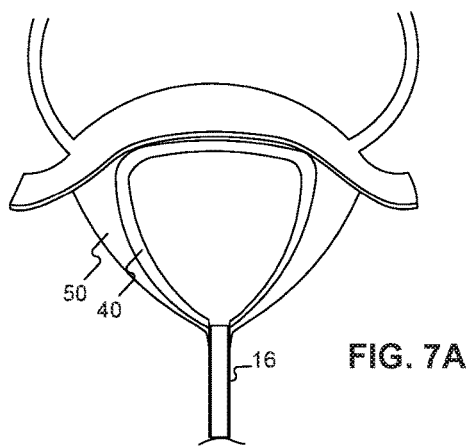
FIG. 7A illustrates a medical device being inserted into a bladder through an outer sheath, according to an embodiment of the disclosure.
Figure 7B:
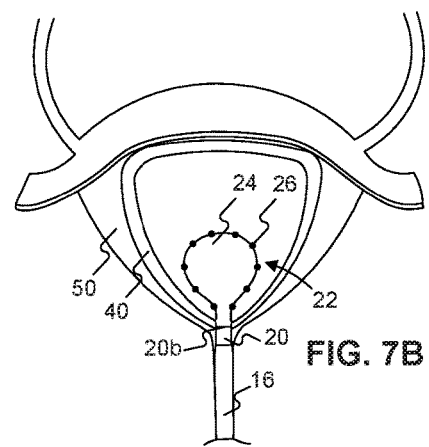
FIG. 7B illustrates an end effector assembly of the medical device being positioned in the bladder and a first expandable member of the end effector assembly being in a partially collapsed configuration.
Figure 7C:
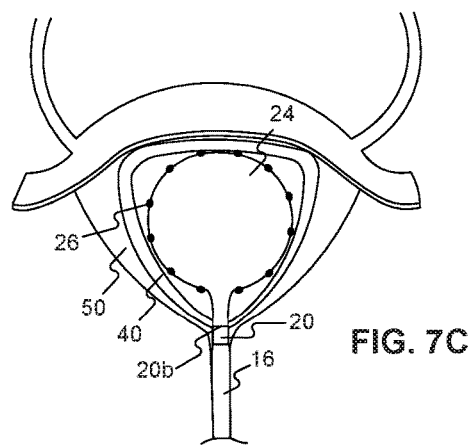
FIG. 7C illustrates the first expandable member of the end effector assembly being in an expanded configuration.

FIGS. 7A-7E illustrate a method for treating a bladder in accordance with an embodiment of the present disclosure. In particular, FIGS. 7A-7C illustrate a method for treating bladder overactivity by separating two tissue layers within the bladder wall. Those of skill in the art will readily recognize that the principles of the disclosed embodiments may have utility relative to any organ within a patient's body, such as the uterus, stomach, lung, etc.

Referring to FIGS. 7A and 7B, medical device 10 is inserted into the urethra of a patient after bladder emptying, and may be advanced to bladder 50 through outer sheath 16 (FIG. 7A). Once a distal end of outer sheath 18 is positioned in bladder 50, end effector assembly 22 is advanced distally out of outer sheath 18 (FIG. 7B). This may be achieved by, for example, pushing elongate member 20 distally relative to outer sheath 16, or polling outer sheath 18 proximally relative to elongate member 20. Any suitable actuator on handle portion 18 may be used to effect deployment of end effector assembly 22.

Once end effector assembly 22 has been removed from outer sheath 16, inflation fluid is delivered through lumen 28 to first expandable member 24 to inflate first expandable member 24 from a partially collapsed configuration (FIG. 7B) to an expanded configuration (FIG. 7C). When fully expanded, expandable member 24 may have a substantially spherical shape, positioning each injection unit 26 adjacent an interior surface of bladder wall 40 (FIG. 7C). It is understood that the expandable member may have alternative shapes, such as shapes mimicking the shape of the organ the medical device 10 is being inserted into. Further expansion of first expandable member 24 causes injector 30 of each injection unit 28 to pierce bladder wall 40. In some embodiments, injector 30 may be configured to pierce the bladder wall 40 as deep as the mucosa-detrusor junction without penetrating the detrusor muscle. The penetration depth may be monitored in a number of ways. For example, injector 30 may be dimensioned to penetrate bladder wall 40 and deliver material at a predetermined depth (i.e., injector 30 may be a single predetermined length). Additionally and/or alternatively, injector 30 may be provided with radiopaque markers that can be visualized as injector 30 is penetrating tissue. In further embodiments, the device may include an actuator that may enable operator to simultaneously advance injectors 30 in known increments. Alternatively, the injector 30 may include a flange, stop, or shoulder to press up against tissue to control the depth of penetration of the injector 30.

The procedure continues with the physician advancing injection mechanism 34 within lumen 28 of elongate member 20. In particular, the physician may move tube 38 of actuation mechanism 34 relative to elongate member 20 in order to advance second expandable member 36 from a retracted position within lumen 28 of elongate member 20 to a deployed position within interior space 24b of first expandable member 24. The mechanisms for extending second expandable member 38 into interior space 24b of first expandable member 24 are well known in the art and need not be discussed here.

Once second expandable member 38 is in the deployed position, inflation fluid may be delivered through lumen 39 of tube 38 to inflate second expandable member 36 from a collapsed configuration to an expanded configuration (FIGS. 7D and 7E). As second expandable member 36 expands, second expandable member 38 may come into contact with the one or more dispensers 32 associated with the one or more injection units 28. Further expansion of second expandable member 38 may exert a force on dispensers 32. Upon application of sufficient force, the impermeable membrane 32a of each dispenser 32 may rupture injecting material from dispensers 32 into injectors 30 for delivery between tissue layers of the bladder. It is understood that dispensers 32 may take any number of shapes other than that disclosed in the figures, such as, for example, a bellows shape.

The injected material or compound may be a liquid (e.g., saline), a gel, or a liquid/gel that cures into a solid or fluid. For example, the material may include a hydrogel (e.g., PEG, hyaluronic acid, polyacrylamide gel, chitosan, sodium alginate, PLA or hydrogel mixture) which, after injection, may be cured by cross-linking as is known in the art. The injected material may have any desired composition, viscosity, and/or biodegradability characteristics so as to permit the injected material such as a cured hydrogel, to carry and deliver a drug over an extended period of time, such as, for example, several months or years. Further, the injected material, such as a hydrogel, may include high expansion properties (e.g. expanding between approximately five to approximately ten times its original volumetric size). As such, a large physical barrier may be achieved while using a small volume/amount of the injected material. Additionally, such a hydrogel may be absorbable into bladder wall 40.

The material may be injected into a space between two tissue layers 40a, 40b in bladder wall 40 to separate and maintain the two layers. For example, the material may be injected between the mucosal layer 40b and the detrusor layer 40a to create a semi-permanent barrier between the layers that may prevent the detrusor muscle contraction and expansion. The injections may be performed at sites spaced equidistantly from one another along bladder wall 40 so as to uniformly treat bladder 50. It is contemplated, however, that first expandable member 24 may be partially expanded, and end effector assembly 22 may be positioned adjacent a site of abnormal activity, to selectively treat that portion of bladder 50.

Figure 8:
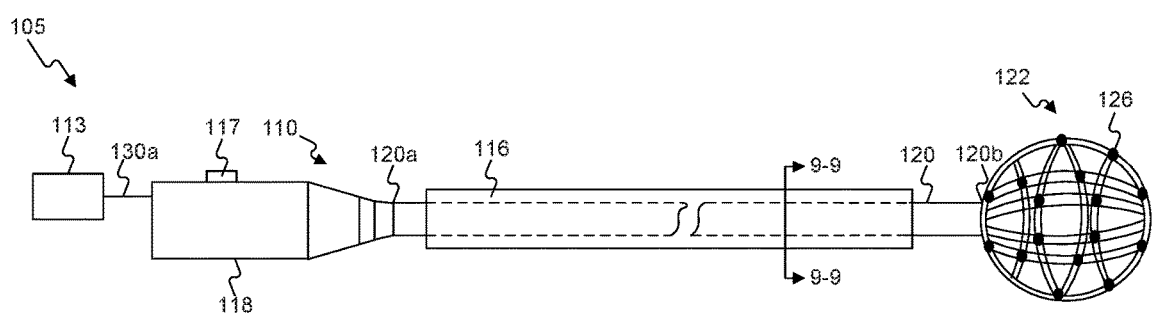
FIG. 8 illustrates a system for treatment of a bladder including a medical device, according to a second embodiment of the disclosure.

FIG. 8 illustrates an exemplary system 105 according to another embodiment of the present disclosure. System 105 has similar components as the embodiment discussed above. In this embodiment, however, at least one external dispenser 113 may be connected to medical device 110 via injector 130. Dispenser 113 maybe a syringe, vial, or other known container configured to retain the material to be injected between tissue layers of the bladder.

In the exemplary embodiment illustrated in FIG. 8, medical device 110 include an elongate member 120, a handle portion 118, and an end effector assembly 122. Elongate member 120 has a proximal end 120a and a distal end 120b. Handle portion 118 is disposed at proximal end 120a of elongate member 120 and includes at least one actuator 117. End effector assembly 122 is disposed at distal end 120b of elongate member 120. End effector assembly 122 includes one or more injection units 126.

Figure 9:
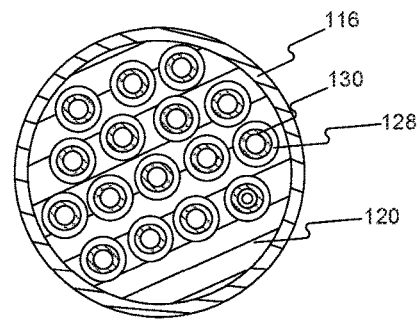
FIG. 9 is a cross-section of the medical device along line 9-9 of FIG. 8.

FIG. 9 is a cross-section of elongate member 120 along lines 9-9 in FIG. 8. As discussed above, elongate member 120 may be a solid rod or tube, made from any suitable biocompatible material known to one of ordinary skill in the art having sufficient flexibility to traverse an anatomical lumen such as a urethra. In this embodiment, elongate member 120 includes one- or more lumens 128 extending from proximal end 120a of the elongate member 120 to distal end 120b of the elongate member 120. It is to be understood that lumens 128 may have any size, cross-sectional area, shape, and/or configuration. Although the depicted embodiment includes sixteen lumens, elongate member 120 may include a greater or lesser number of lumens 128. It is to be understood that the number of lumens 128 may depend on the number of injection units 126 on end effector assembly 122.

FIG. 10 depicts a side view of end effector assembly 122. As shown in FIG. 10, end effector assembly 122 extends distally from distal end 120b of elongate member 120, and includes a plurality of legs 124a extending from a proximal end 122a of end effector assembly 122 to a distal end 122b of end effector assembly 122 in some embodiments, end effector assembly 122 may also include one or more circumferentially extending legs, such as legs 124b. In this disclosure, descriptions of legs 124a also pertain to legs 124b, and vice versa.

End effector assembly 122 may he made out of the same piece of material as elongate member 120. Alternatively, end elector assembly 122 may be fabricated independently by any known means and may be made integral with elongate member 120 through connection of a proximal end 122a of the end effector assembly 122 to a region of elongate member 120, such as the distal end 120b of elongate member 120. The connection of proximal end 122a of end effector assembly 120 may be accomplished through any suitable means of fixedly connecting end effector assembly 122 to elongate member 120. For example, possible connections may include, but are not limited to welding, soldering, and/or crimping.

End effector assembly 122 may have any shape and/or configuration and may be any desired dimension that can be received in a bladder. In the exemplary embodiment shown in FIG. 10, legs 124a are configured so that end effector assembly 122 forms a three-dimensional sphere in an expanded state. Legs 124*a* may be constructed from a material such as, for example, elastic, a shape memory, or super elastic material so that legs 124*a* may collapse to have a smaller cross-section in a collapsed state.

Although FIG. 10, shows that that end effector assembly 122 comprises six legs 124*a* extending from proximal end 122*a* of end effector assembly 122 to distal end 122*b* of end effector assembly 122 (and four circumferential legs 124*b*), end effector assembly 122 may include any number of legs 124*a* (or 124*b*) having any desired pattern and/or configuration. For example, legs 124*a* may form a cylinder, square, semi-circle, rectangle, or any other suitable shape. In addition, legs 124*a* may be any cross-sectional shape known in the art including, but not limited to, circular, square, or ovular.

Referring to FIG. 11, each leg 124*a* of end effector assembly 122 includes one or more lumens 125 located longitudinally therein. Lumens 125 may have any size, cross-sectional area, shape, and/or configuration. Each lumen 125 is in communication with a corresponding lumen 128 of elongate member 120, and extends from proximal end 122*a* of end effector assembly 122 to an exit aperture 127 on leg 124*a*.

An individual injection unit 128 is fixed in each exit aperture 127. In the exemplary embodiment, injection unit 128 includes a catheter 132 and an injector 130 disposed therein. Catheter 132 may include a proximal end (not shown) terminating proximally of exit aperture 127 in lumen 125, and a distal facing surface 132*b* flush with, or protruding from, exit aperture 127. Distal facing surface 132*b* may be configured to contact tissue. It is contemplated that in some embodiments, catheter 132 may move relative to exit aperture 127. In these embodiments, catheter 132 may extend proximally through lumen 125 of legs 124*a* and a corresponding lumen 128, and may be connected to a push and/or pulling mechanism in handle portion 118.

Referring to FIG. 12, catheter 132 includes a lumen 133 extending longitudinally therein. Lumen 133 may have any size, cross-sectional area, shape, and/or configuration, and may extend from the proximal end (not shown) to an aperture 133*b* on distal facing surface 132*b*. In the exemplary embodiment, aperture 133 may have a substantially ovular shape to permit lateral movement of injector 130. It will be understood, however, that aperture 133 may have any other size, shape, and/or configuration.

Injector 130 may be positioned in lumen 133 of catheter 132. In particular, injector 130 may extend proximally from catheter 132 through lumen 125 of leg 124*a*, a corresponding lumen 128 of elongate member 120, and handle portion 118 (FIG. 8), injector 130 may be a conventional needle, including, for example, a micro-needle, having a proximal end 130*a*, a sharpened distal point 130*c*, and a hollow interior. Referring back to FIG. 8, proximal end 130*a* may extend proximally of handle portion 118 for coupling to dispenser 113. In some embodiments, proximal end 130*a* may include a luer fitting or any other fitting to facilitate coupling between proximal end 130*a* and dispenser 113.

Figure 13A:
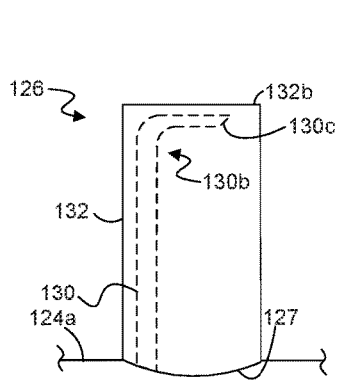
FIG. 13A is a partial side view of the injection unit with an injector in a retracted configuration.
Figure 13B:
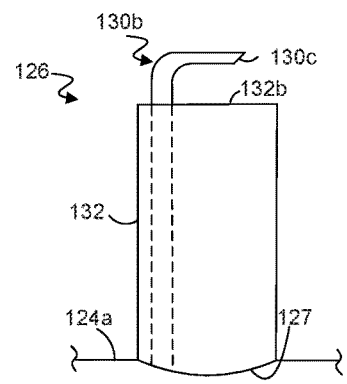
FIG. 13B is a partial side view of the injection unit with the injector in a first position in the deployed configuration.
Figure 13C:
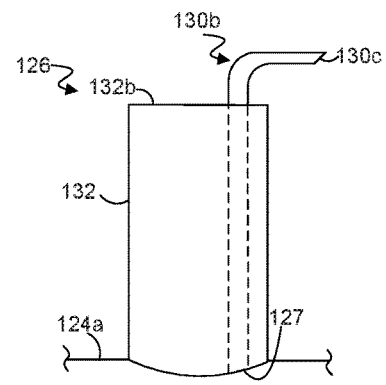
FIG. 13C is a partial side view of the injection unit with the injector in a second position in the deployed configuration.

Referring to FIGS. 13A-13C, injector 130 may include a distal portion 130*b*. The particular shape, configuration, and/or dimensions of distal portion 130*b* of injector 130 may be selected to penetrate issue and deliver material at a predetermined depth. In the exemplary embodiment, distal portion 130*b* of injector 130 may have a right angle bend and terminate at distal point 130*c*, it will be understood that the bend of distal portion 130*b* may be abrupt or curved and may have an angle greater or lesser than 90°. Distal portion 130*b* may have any other shape and/or configuration that may penetrate tissue at the desired depth.

Injector 130 may be operatively connected to the at least one actuator 117 on handle portion 118 to move distal portion 130*b* of injector 130 longitudinally relative to lumen 133 from the retracted configuration in FIG. 13A to the deployed configuration in FIG. 13B. In the deployed configuration, distal portion 130*b* of injector 130 may extend beyond distal facing surface 132*b* of catheter 132 (FIG. 13B). The same actuator 117 or a different actuator 117 may be configured to move injector 130 laterally within lumen 133 and aperture 133*b* between a first position (FIG. 13B) and a second position (FIG. 13C) to facilitate placement of distal point 130*c* between tissue layers of the bladder. In some embodiments, distal portion 130*b* of injector 130 and/or aperture 133*b* may include one or mere retaining mechanisms to retain distal portion 130*b* in the second position during the injection procedure.

Figure 14A:
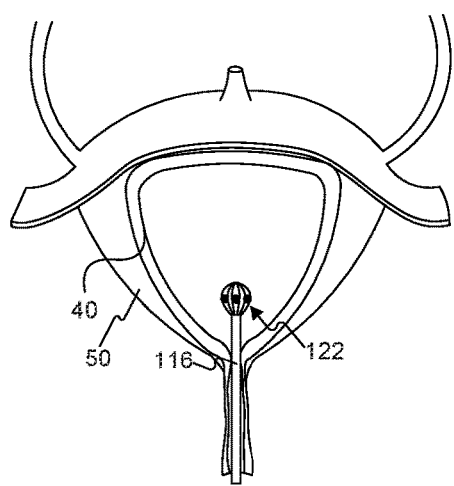
FIG. 14A illustrates an end effector assembly of the medical device being positioned in the bladder, according to another embodiment of the disclosure.
Figure 14B:
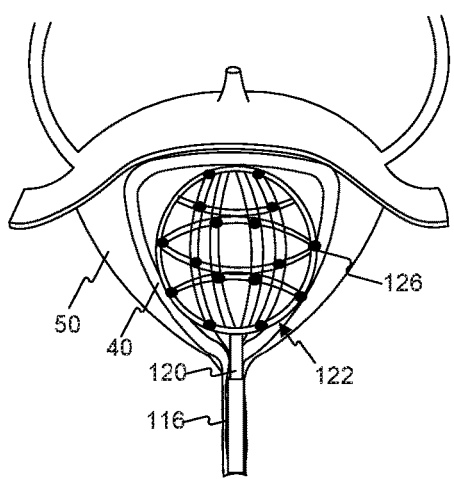
FIG. 14B illustrates the end effector assembly in an expanded configuration.

A method of treating a bladder in a patient will now be described. Referring to FIGS. 14A and 14B, medical device 110 may be inserted into the urethra of a patient after bladder emptying, and may be advanced to bladder 60 through outer sheath 118 (FIG. 14A). Once a distal end of outer sheath 116 is positioned in bladder 50, end effector assembly 122 may be advanced distally out of outer sheath 118. This may be achieved by, for example, pushing elongate member 120 distally relative to outer sheath 118, or pulling outer sheath 118 proximally relative to elongate member 120.

Once end-effector assembly 122 has been removed from outer sheath 118, end effector assembly 122 may be expanded to an expanded configuration (FIG. 14B). In some embodiments, end effector assembly 122 may self-expand. In other embodiments, an expansion mechanism such as, for example, a balloon may be used to facilitate expansion of end effector assembly 122. When fully expanded, end effector assembly 122 may have a substantially spherical shape, positioning each injection unit 128 adjacent an interior surface of bladder wall 40.

Figure 15A:
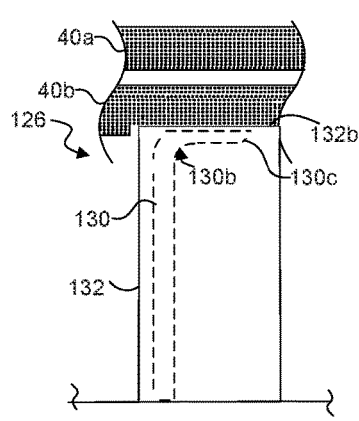
FIG. 15A illustrates an individual injection unit contacting the bladder wall.
Figure 15B:
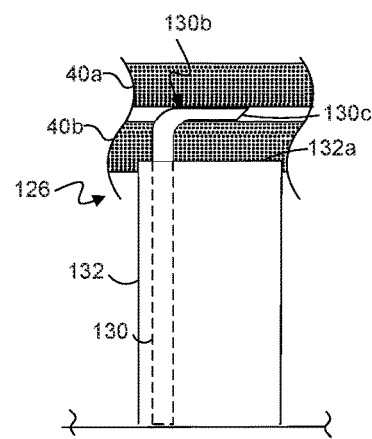
FIG. 15B illustrates an injector being deployed from a catheter of the injection unit with the injector in a first position.

The procedure continues with the physician inserting distal portion 130*a* of each injector 130 into bladder wall 40. In particular, the physician may engage the at least one actuator 117 on handle portion 118 to move injectors 130 relative to lumens 128 in elongate member 120, lumens 125 in legs 124*a* (or legs 124*b*), and lumens 133 in catheters 132 in order to advance distal portion 130*b* of injectors 130 from a retracted position within lumen 133 of catheter 132 to a deployed position distal to a distal facing surface 132*b* of catheter 132 (FIGS. 15A and 15B).

As distal portion 130*b* extends out of aperture 133*b*, distal point 130*c* may be configured to penetrate tissue. As discussed in the embodiment described above, it may be desirable to penetrate tissue and inject material at a predetermined depth. For example, injector 130 may be configured to penetrate the bladder wall 40 as deep as the mucosa-detrusor junction without penetrating the detrusor muscle. The penetration depth may be monitored in a number of ways. For example, distal portion 130*b* of injector 130 may be shaped and/or dimensioned to piece bladder wall 40 to a desired depth so that material may be delivered at the predetermined depth (i.e., between the detrusor layer and the mucosal layer). Additionally and/or alternatively, injector 130 may be provided with radiopaque markers that can be visualized as distal portion 130*b* is penetrating tissue. In further embodiments, actuator 117 may enable operator to advance injectors 130 simultaneously or individually in known increments.

Figure 15C:
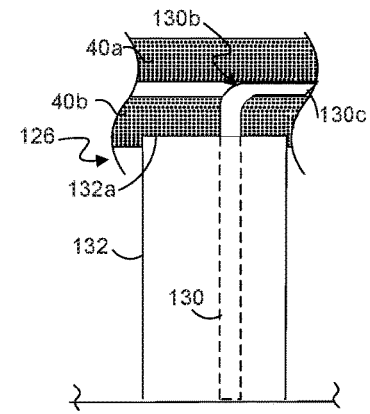
FIG. 15C illustrates the injector in a second position.

Once injectors 130 are in the deployed position, the same actuator 117 or a different actuator 117 may be configured to drive distal portion 130b of each injector 130 laterally in apertures 133b. Lateral movement of injector 130 between a first position shown in FIG. 15B and a second position shown in FIG. 15C may facilitate positioning of distal point 130c between mucosal layer 40b and the detrusor layer 40a of bladder wall 40. Material may then be injected from dispenser 113 through the proximal end 130a of each injector 130 to deliver the material between the two tissue layers.

In some embodiments, the physician may uniformly treat bladder 50 by simultaneously delivering material through all of the injection units 126. In other embodiments, the physician may selectively deliver material through one or more specific injection units 128 to treat areas of abnormalities within bladder 50. In these embodiments, medical device 110 may include a sensing element to detect an area of abnormal function in the bladder and transmit the data via a cable or wirelessly to the physician.

As in the prior embodiment, the material may be delivered between the mucosal layer 40b and the detrusor layer 40a to separate and maintain the two layers. In additional and/or alternative embodiments, the medical device may include a suction lumen positioned at a distal end 120b of elongate member 120, a distal end 122b of end effector assembly 122, and/or in each catheter 132 to assist in the lifting of tissue layers through suction to separate the two tissue layers. The suction procedure is followed with fluid/material insertion between the layers.

Figure 16A:
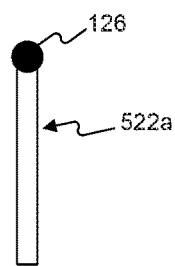
Figure 16B:
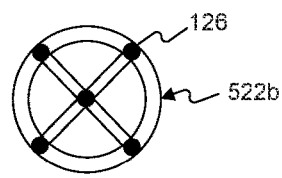
Figure 16C:
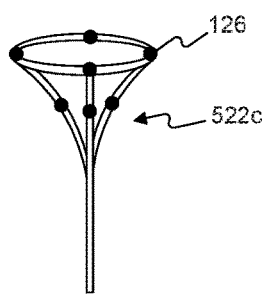
Figure 16D:
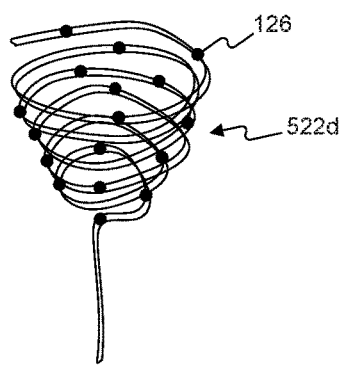
Figure 16E:
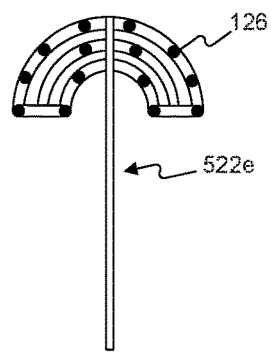

Alternative non-limiting examples of end effector assemblies having various shapes and/or distal configurations are shown in FIGS. 16A-16E. FIGS. 16A and 16D depict end effector assemblies having wire configurations. In particular, end effector assembly 522a, as shown in FIG. 16A, may have a substantially linear configuration. A single end effector unit 126 may be disposed at a distal end of end effector assembly 522a. In another embodiment, end effector assembly 522d, as shown in FIG. 16D, may have a helical configuration preferably tapering from a larger diameter at a distalmost end thereof to a smaller diameter proximally of the distalmost end thereof. A kink may be disposed adjacent a proximal end of end effector assembly 522d. FIG. 16C depicts an end effector assembly 522c having a plurality of legs curving away from a longitudinal axis of end effector assembly 522c. FIGS. 16B and 16E depict end effector assemblies having a mesh configuration. In particular, end effector assembly 522b, as shown in FIG. 16B, may have a circular shape. And in yet another embodiment, end effector assembly 522e, as shown in FIG. 16E, may have a semi-circular shape. End effector assemblies 522c and 522e may be additionally planar, concave, or convex.

Alternative embodiments of injection units will now be described, it will be noted that at least certain aspects of the embodiments discussed below may be combined with other aspects of the embodiments discussed above. For example, one or more of the following injection units may be provided on one of the end effector assemblies discussed above to position the injection units within the bladder.

Figure 17A:
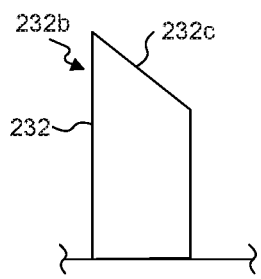
FIG. 17A is a partial side view of a catheter of an injection unit, in accordance with another embodiment of the disclosure.
Figure 17B:
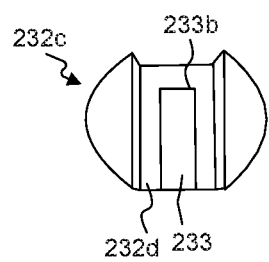
FIG. 17B is a perspective view of a distal facing surface of the catheter.
Figure 17C:
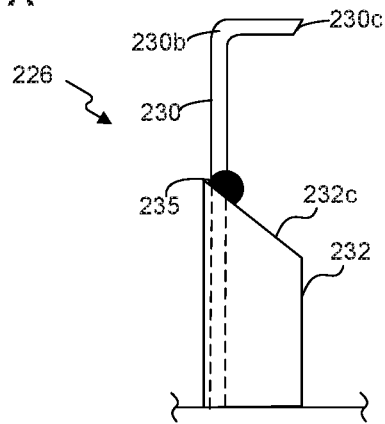
FIG. 17C is a partial side view of the catheter and an injector disposed in the catheter.

FIGS. 17A-17C illustrate an injection unit 228. Injection unit 228 includes a catheter 232 and an injector 230. Catheter 232 may have a proximal end (not shown), a distal end 232b, and a lumen 233 extending therethrough. In the exemplary embodiment, distal end 232b of catheter 232 may be wedge shaped. It is contemplated that distal end 232b may be sharpened to facilitate insertion into tissue.

Lumen 233 may terminate at an aperture 233b on a distal facing surface 232c of catheter 232. Distal facing surface 232c may include one or more features to drive injector 230 to a desired position and orient injector 230 relative to catheter 232. For example, distal facing surface 232c may include a ramp 232d adjacent aperture 233b. Ramp 232d may be shaped to drive injector 230 from a first position on one end (side) of distal end 232b of catheter 232 to a second position on an opposing end (side) of distal end 232b of catheter 232, in particular, ramp 232 may be disposed in a plane that is not perpendicular to a longitudinal axis of catheter 232 (FIGS. 17A). Furthermore, ramp 232d may be sized and shaped to interact with one or more aligning members 235 on injector 230 to orient injector 230 relative to catheter 232. For example, the width of ramp 232d may be sized to receive an aligning member 235 and to prevent rotation of the aligning member 235 and injector 230.

Figure 18A:
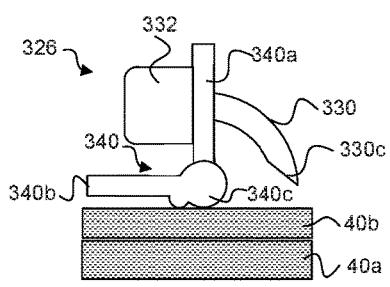
FIG. 18A is schematic view of an injection unit, in accordance with another embodiment of the disclosure.
Figure 18B:
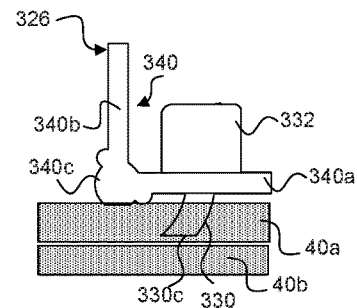
FIG. 18B is a schematic view of the injection unit of FIG. 18A, with an injector inserted into tissue of the bladder wall.
Figure 18C:
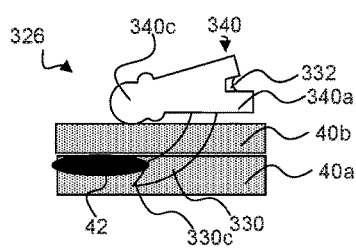
FIG. 18C is a schematic view of the injection unit of FIG. 18A, with a collapsed dispenser.
Figure 18D:
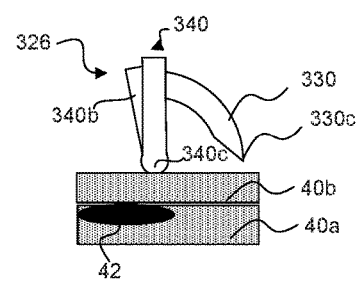
FIG. 18D is a schematic view of the injection unit of FIG. 18A, with the injector retracted from the tissue.

FIGS. 18A-18C illustrate an injection unit 326. In accordance with another embodiment of the disclosure, injection unit 326 may include a frame 340 having a first arm 340a and a second arm 340b pivotably connected to the first arm 340a via a pivot 340c. An injector 330 may be provided on first arm 340a. In particular, injector 330 may be fixed to a surface of first arm 340a and may extend in a direction generally perpendicular to first arm 340. Frame 340 may be a positioning mechanism configured to position injector 330 adjacent tissue and facilitate insertion of injector 330 into tissue.

In this embodiment, injector 330 may be a curved needle, including, for example, a micro-needle, having a sharpened distal point 330c and a hollow interior, injector 330 may be sized to penetrate tissue and inject material at a predetermined depth. It is understood that injector 330 may have any other size and/or configuration to penetrate tissue at the predetermined depth.

A dispenser 332 may be mounted be first and 340a opposite to injector 330. Dispenser 332 may be in fluid communication with injector 330 via an aperture (not shown) in first arm 340a. In this embodiment, dispenser 332 may be an elastomeric fluid container retaining material to be injected between two tissue layers of the bladder. Dispenser 232 may have an impermeable membrane or a collapsible wall configured to collapse on application of sufficient force by an injection mechanism such as, for example, second arm 340b. As dispenser collapses, the material may be introduced into injector 330.

Injection unit 328 may be introduced into the bladder and positioned adjacent bladder wall 40 using the procedures discussed above. Injection unit 326 may be placed adjacent the bladder wall 40 with second arm 340b parallel to the detrusor layer 40a and mucosal layer 40b of bladder wail 40, in order to insert injector 330 into tissue, frame 340 may be rotated, so that second arm 340b is generally perpendicular to the tissue. Any known actuation mechanism, such as an electrical actuator or linear actuator, may be attached to frame 340 and may be configured to apply sufficient force to rotate frame 340. As frame 340 rotates, distal point 330c of injector 330 may be inserted into the tissue.

The procedure may continue by collapsing dispenser 332. For example, the same actuation mechanism or a different actuation mechanism may apply a force to second arm 340b to pivot second arm 340b relative to first arm 340a about pivot 340c. As second arm 340b pivots towards the first arm 340a, second arm 340b may apply sufficient force to collapse dispenser 332. In this manner, material 42 may be injected into injector 330 for delivery between tissue layers of the bladder. Injector 330 may be removed by rotating first arm 340a, so that first arm 340a and second arm 340b are generally perpendicular to the tissue.

Figure 19A:
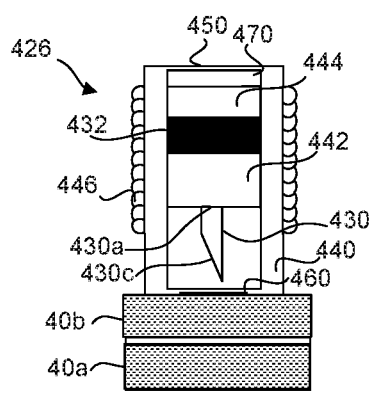
FIG. 19A is a schematic view of an injection unit with an injector in a refracted position, in accordance with another embodiment of the disclosure.
Figure 19B:
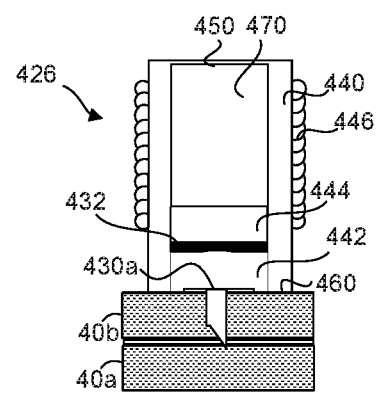
FIG. 19B is a schematic view of the injection unit of FIG. 19B, with the injector in a deployed position.

FIGS. 19A-19B illustrate an injection unit 428 in accordance with another embodiment of the disclosure. In this embodiment, injection unit 426 includes a housing 440 having a closed top 450, an open bottom 480, and a space 470 extending therebetween. The closed top 450 may be closed by, for example, a cap. In some embodiments, the cap may include a breathable membrane. The open bottom 460 may be configured to be oriented towards tissue and contact tissue.

A first magnetic disk 444 may be disposed in space 470, and may be configured to move relative to housing 440 between the closed top 450 and open bottom 480. The first magnetic disk 444 may sealingly engage the inner walls of housing 440. For example, first magnetic disk 444 may have radial seals, such as, for example an O-ring or a lip seal, to engage housing 440. A second magnetic disk 442 may be disposed between the first magnetic disk 444 and the open bottom 460. Second magnetic disk 442 may have similar seals.

An injector 430 may be fixed to second magnetic disk 442. In particular, a proximal end 430a of injector 430 may extend through an aperture (not shown) in second magnetic disk 442 and may be fixed to the aperture. In this embodiment, injector 430 may be a cylindrical needle, such as, for example, a micro-needle, having a sharpened distal point 430c and a hollow interior, injector 430 may be sized to penetrate tissue and inject material at a predetermined depth. It is understood that injector 430 may have any other size and/or configuration to penetrate tissue.

A dispenser 432 may be disposed between the first magnetic disk 444 and the second magnetic disk 442. In this embodiment, dispenser 432 may be a collapsible dispenser retaining fluid in, for example, a collapsible, impermeable membrane. The membrane may be configured to collapse and rupture on application of sufficient force to inject the material into proximal end 430a of injector 430.

Housing 440 may further include coil windings 446 disposed on an outer surface of housing 440. Coil windings 446 may attach to an electrical wire (not shown) that may extend proximally through a medical device to a source of electricity, in operation, housing 440, first magnetic disk 444, second magnetic disk 442, and coil windings 446, together, may be a positioning mechanism configured to position injector 430 adjacent tissue and facilitate insertion of injector 330 into tissue. In particular, current may pass through the coil windings 446 inducing an electrical field whose electromotive force may be used to drive first magnetic disk 444 and second magnetic disk 442 downward. The force may be sufficient to insert injector 430 into the adjacent tissue.

After injector 430 has been inserted into tissue, the electromotive force may continue to drive the first magnetic disk 444 downward. First magnetic disk 444 may act as an injection mechanism by applying sufficient pressure on dispenser 432 to rupture dispenser 432 disposed between the first magnetic disk 444 and the second magnetic disk 442. In this manner, material may be injected into injector 430 for delivery between two tissue layers of the bladder.

The same deployment may be accomplished with an electrical coil and a spring recoil. In particular, current may be applied to the coil windings of the injection unit in/only one direction to insert injector into tissue and inject material between the two tissue layers. The recoil spring (placed between second magnetic disk 442 and open bottom 460) may then retract injector 430. In another embodiment, deployment may be accomplished with a compressed fluid end a spring recoil. In this embodiment, the compassed fluid, applied to first magnetic disk 444, may be configured to apply sufficient force to deploy injector 430 and inject the material. As in the embodiment described above, the recoil spring may retract injector 430 once the fluid pressure is relieved.

Other injection units are contemplated. For example, in other embodiments, each of the one or more injection units may have a micro-needle array in place of a single injector. In this manner, the injection unit may target a wider area of tissue within the bladder. In additional and/or alternative embodiments, the material may be dispersed through the injector (or needle array device) onto tissue adjacent the injection units without perforating the bladder wall. This procedure may be performed for a set duration at varying amplitudes to increase the permeability of the mucosal layer (e.g., the urothelium).

Other embodiments of the disclosure will be apparent to those skilled in the art from consideration of the specification and practice of the invention disclosed herein, it is intended that the specification and examples be considered as exemplary only, with a true scope and spirit of the invention being indicated by the following claims.

In some embodiments, the fluid dispenser 32 does not rupture, but rather fluid is releasable upon application of pressure which forces fluid through pores in the wall of the dispenser. The pores may be elastic or nonelastic, and may be holes, slots, or slits. Alternatively, the fluid dispenser 32 may remain sealed and the needle includes pores, slots, holes, or slits that open with increased pressure and convey fluid from the dispenser to the tissue.

What is claimed is:

1. A device for treating a bladder, comprising:
   a shaft having a proximal end, a distal end, and a plurality of lumens;
   a spherical end effector assembly extending distally from the distal end of the shaft, the end effector assembly defining a plurality of apertures, wherein each aperture is in communication with a corresponding lumen of the shaft; and
   an injection unit positioned in each aperture of the end effector assembly to direct delivery of material from the end effector assembly;
   wherein each injection unit includes:
      a frame including a first arm;
      an injector; and
      a dispenser, and
   wherein the injector is coupled to a surface of the first arm and extends away from the first arm, and wherein the dispenser is coupled to the first arm on a side opposite to the injector.

2. The device of claim 1, further comprising an actuation mechanism.

3. The device of claim 1, wherein the injector is a needle having at least a curved portion, a distal point, and a hollow interior.

4. The device of claim 1, wherein the dispenser is directly coupled to the first arm opposite to the injector.

5. The device of claim 4, wherein the dispenser is in fluid communication with the injector via an aperture in the first arm.

6. The device of claim 4, wherein the dispenser is an elastomeric fluid container.

7. The device of claim 1, wherein the injector is directly fixed to a surface of the first arm and extends perpendicular to the first arm.

8. The device of claim 7, wherein the injector is a needle having at least a curved portion, a distal point, and a hollow interior.

9. The device of claim 8, wherein the needle is a microneedle.

10. A device for treating a bladder, comprising:
a shaft having a proximal end, a distal end, and a plurality of lumens;
an end effector assembly extending distally from the distal end of the shaft, the end effector assembly defining a plurality of apertures, wherein each aperture is in communication with a corresponding lumen of the plurality of lumens of the shaft; and
an injection unit at least partially positioned within each aperture of the end effector assembly to direct delivery of material from the end effector assembly;
wherein each injection unit includes:
a frame including a first arm and a second arm connected to the first arm via a pivot;
an injector coupled to the first arm and extending away from the first arm; and
a dispenser coupled to the first arm opposite to the injector and in fluid communication with the injector via an arm aperture in the first arm.

11. The device of claim 10, wherein the dispenser is in fluid communication with the injector via an aperture in a portion of the frame.

12. The device of claim 10, wherein the injector is a needle having at least a curved portion, a distal point, and a hollow interior.

13. The device of claim 10, wherein the injector is directly coupled to a surface of the first arm and extends at least partially perpendicular to the first arm; and
wherein the dispenser is mounted on and directly coupled to the first arm opposite to the injector.

14. The device of claim 13, wherein the injector is a needle having at least a curved portion, a distal point, and a hollow interior.

15. The device of claim 14, further comprising an actuation mechanism, wherein the actuation mechanism causes the frame to rotate or causes the second arm to pivot and apply force to the dispenser.

16. The device of claim 14, wherein the needle is a microneedle.

17. A device for treating a bladder, comprising:
a shaft having a proximal end, a distal end, and a plurality of lumens;
a spherical end effector assembly extending distally from the distal end of the shaft, the end effector assembly defining a plurality of apertures, wherein each aperture is in communication with a corresponding lumen of the shaft; and
an injection unit positioned in each aperture of the end effector assembly to direct delivery of material from the end effector assembly;
wherein each injection unit includes:
a frame, including a first arm and a second arm connected by and movable relative to a pivot;
an injector, wherein the injector includes a curved portion that is directly coupled to and extends from a first side of the first arm; and
a dispenser, wherein the dispenser is directly coupled to a second side of the first arm opposite to the first side.

18. The device of claim 17, wherein the first arm is pivotable via the pivot such that the curved portion of the injector penetrates tissue when the first arm abuts the tissue.

19. The device of claim 18, wherein the second arm is pivotable between at least a first position perpendicular to the first arm and a second position at an acute angle relative to the first arm to apply pressure to the dispenser.

20. The device of claim 19, wherein the dispenser includes an impermeable membrane or a collapsible wall, and wherein pressure applied to the dispenser breaks or collapses the impermeable membrane or the collapsible wall to deliver a treatment fluid through the curved portion of the injector.

* * * * *